United States Patent [19]

Dudrick

[11] Patent Number: 5,248,688
[45] Date of Patent: * Sep. 28, 1993

[54] METHOD AND SUBSTRATE COMPOSITION FOR TREATING ATHEROSCLEROSIS

[75] Inventor: Stanley J. Dudrick, Houston, Tex.

[73] Assignee: Dudrick Medical Research Fund I, Ltd., Houston, Tex.

[*] Notice: The portion of the term of this patent subsequent to Jul. 16, 2008 has been disclaimed.

[21] Appl. No.: 663,607

[22] Filed: Mar. 4, 1991

Related U.S. Application Data

[63] Continuation of Ser. No. 287,620, Dec. 16, 1988, Pat. No. 5,032,608, which is a continuation of Ser. No. 905,934, Sep. 10, 1986, abandoned.

[51] Int. Cl.⁵ ............... A61K 31/415; A61K 31/40; A61K 31/195
[52] U.S. Cl. .................... 514/396; 514/419; 514/423; 514/561; 514/562; 514/565; 514/824
[58] Field of Search ............... 514/396, 419, 423, 561, 514/562, 565, 824

[56] References Cited

U.S. PATENT DOCUMENTS

| | | | |
|---|---|---|---|
| 2,411,897 | 12/1947 | Sahyun | 167/65 |
| 2,457,820 | 1/1949 | Howe et al. | 167/65 |
| 2,965,542 | 12/1960 | Castaigne | 167/65 |
| 3,574,857 | 4/1971 | Cevallos | 424/319 |
| 3,764,703 | 10/1973 | Bergstrom et al. | 434/319 |
| 3,832,465 | 8/1974 | Ghadimi | 514/651 |
| 3,920,838 | 11/1975 | Flatt et al. | 424/319 |
| 3,950,529 | 4/1976 | Fisher et al. | 424/273 |
| 4,103,021 | 7/1978 | Carr | 429/278 |
| 4,167,562 | 9/1979 | Evers | 424/153 |
| 4,430,338 | 2/1984 | Jansen et al. | 424/274 |
| 4,532,129 | 7/1983 | Comi et al. | 424/94 |
| 4,604,286 | 8/1986 | Kawajiri | 424/149 |
| 4,812,441 | 3/1989 | Kawai et al. | 514/824 |

FOREIGN PATENT DOCUMENTS 2149394 6/1985 United Kingdom.

OTHER PUBLICATIONS

Dudrick, D., et al. J. Parenteral and Enteral Nutr. 9, No. 1 (1985), p. 116.
Sugano, M. et al. Ann. Nutr. Metab., 28 (1984), 192–99.
Redgrave, T. G., et al., Atherosclerosis 52(1984), 349–51.
Sugiyama, K., et al., J. Nutr. Sci. 32(6) 623–33 (1986).
Schwartz, R. G. et al. J. Clin. Invest., 75 (1985), 1204–11.
Yagasaki, K., et al. Nutr. Reports Intnl. 34, No. 1 (Jul. 1986), 59–66.
Kramer, J. H., et al. Am. J. Physiol., 240 (Heart Cir. Phy. 9) (1981) H238–46.
Azuma, J. et al., Tanrine: Biological Achions and Clinical Perspectives, (1985) 195–213.
Kritschevsky, D., et al., Atherosclerosis, 26 (1977) 397–403.
Kritchevsky, D. et al., Atherosclerosis, 39 (1981) 169–75.
Kritchevsky, D. et al. Atherosclerosis, 41 (1982) 429–31.
Dudrick, S. brochure of USV Labs (1982) "Parenteral Nutrition for Hospitalized Patients, Case Studies in Parenteral Nutrition", No. 3, A Severely Burned Patient.
Dudrick, S. et al., Contemp. Ob/Gyn Special Issue, Update on General Surgery (1983) 95–96, 101–03.

(List continued on next page.)

Primary Examiner—Frederick E. Waddell
Assistant Examiner—Raymond J. Henley, III
Attorney, Agent, or Firm—Winstead Sechrest & Minick

[57] ABSTRACT

A method and substrate composition for treating atherosclerosis are provided. The method involves parenterally administering the substrate composition as an aqueous solution to substantially lower plasma cholesterol and substantially reverse arterial plaque deposition and degenerative changes associated with atherosclerosis. The substrate compositions include mixtures of biologically active levorotatory amino acids as the antiatherosclerotic agent.

23 Claims, 1 Drawing Sheet

OTHER PUBLICATIONS

Dudrick, S., et al., Heart and Lung, 12 No. 2 (1983) 195–201.

Dudrick et al., Fed. Proc., 43, No. 7 (1984) Abstract 3537.

Dudrick, S. Annals of Surgery, 199, No. 6 (1984) 770–81.

Dudrick, S., Arch. Surg. 120 (1985) 721–27.

Katan, M., et al. Atherosclerosis, 43 (1982), 381–92.

Kritchevsky, D. et al. Soy Protein Prev. Athero. Proc. Int. Symp. 4th (1982) 1–11.

West; C., et al. Atherosclerosis, 47 (1983), 263–70.

Boers, G. et al. J. Clin. Inv. 72 (1983) 1971–76.

Perl, M. et al. Psychosomatics, 22 (No. 12) 1981.

Dudrick, S. et al. 13th International Cancer Congress, Part D, 161–70 (1983).

"Crystalline Amino Acid Solutions–Travasol®" in AMA Drug Evaluations (1980) Chicago, 4th edition.

Kritchevsky, D. Atherosclerosis, 49:209–219 (1983).

Sanchez, A. et al., Nutrition Reports Intn. 28(3) 497–508 (1983).

O'Donnell, J. et al., Southern Med. J. 76, No. 11, 1344–8 (1983).

Dudrick, S. et al. Surgery, 64, No. 11 (1986), 134–42.

Dudrick S. J., Parenteral Nutr. 1, No. 1, 23–29 (1977).

Dudrick, S. J. Parenteral and Enteral Nutri. 3, No. 6 (1979) 444–51.

METHOD AND SUBSTRATE COMPOSITION FOR TREATING ATHEROSCLEROSIS

This is a continuation of application Ser. No. 07/287,620, filed Dec. 16, 1988 now U.S. Pat. No. 5,032,608, which is a continuation of Ser. No. 06/905,934, Sep. 10, 1986 now abandoned.

BACKGROUND OF THE INVENTION

The present invention relates generally to compositions and methods for treating atherosclerosis; more particularly, it relates to methods and substrate compositions for treating atherosclerosis whereby the many and varied problems associated with the disease can be arrested, substantially alleviated or even to a certain extent cured. Still more particularly, the present invention utilizes mixtures of biologically active levorotatory (L-form) amino acids to accomplish these results.

In the United States and Western Europe, cardiovascular disease and its associated maladies, dysfunctions and complications are a principal cause of disability and the chief cause of death. One specific entity significantly contributing to this pathophysiologic process is atherosclerosis, which has been generally recognized as the leading health care problem both with respect to mortality and health care costs. During each of the past five years, more than 550,000 deaths have occurred annually in the United States alone as a result of coronary artery disease. Additionally, more than 680,000 hospitalizations for myocardial infarction, the major complication of atherosclerosis, occur annually, and the number is steadily increasing. In recent years, more people in the United States have died as a result of atherosclerosis than of cancer, trauma and infectious diseases combined.

In 1983, the direct health care costs for the management of patients with coronary heart disease in the United States exceeded $8 billion. During the same period the total economic cost to this nation as a result of coronary heart disease as a manifestation of atherosclerosis alone was in excess of $60 billion and for 1987 is estimated to reach $96 billion. These costs do not even reflect the expense required for the management or treatment of the many and varied non-cardiac, atherosclerosis induced conditions.

Atherosclerosis is a disease characterized by the deposition of fatty substances, primarily cholesterol, and subsequent fibrosis in the inner layer (intima) of an artery, resulting in plaque deposition on the surface of, and degenerative changes in, an arterial wall. The ubiquitous arterial fatty plaque is the earliest lesion of atherosclerosis, often found even in children, and is a grossly flat, lipid-rich atheroma consisting of both macrophages (white blood cells) and some smooth muscle fibers. The fibrous plaque representative of the various forms of advanced atherosclerosis has increased intimal smooth muscle cells surrounded by a connective tissue matrix and containing variable amounts of intracellular and extracellular lipid. At the luminal surface of the artery, this plaque or lesion is usually covered by a dense fibrous cap of smooth muscle or connective tissue. Beneath the fibrous cap, the lesions are highly cellular consisting of macrophages, other leukocytes and smooth muscle cells. Deep in this cell-rich region may be areas of cholesterol crystals, necrotic debris and calcification.

If the disease is allowed to progress, it can cause narrowing and obstruction of the lumen of the artery resulting in diminished or occluded blood flow and, consequently, ischemia or infarction of the predominantly affected organ or anatomical part such as the brain, heart, intestine or extremities. The result can be significant loss of function, loss of cellular substance, emergency medical and/or surgical procedures, and significant disability or death. Alternatively, the arterial wall can be severely weakened by the infiltration of the muscular layer with the lipid (cholesterol), inflammatory white blood cells, connective tissue and calcium, resulting in soft and/or brittle areas which can become segmentally dilated (aneurysmal) and rupture or crack leading to organ, limb or even life-threatening hemorrhage.

While the basic definitive cause or causes of atherosclerosis are not fully known or understood, it has been hypothesized that this disorder is related to the plasma cholesterol and lipid levels based on empiric clinical observations of many investigators and medical practitioners. Consequently, one of the currently favored regimens for treating atherosclerosis consists of medication, dietary management, behavior modification and exercise aimed at controlling and reducing the plasma cholesterol levels.

Common medications used to lower plasma cholesterol levels include Atromid-S ® (clofibrate), Choloxin ® (dextrothyroxine sodium), Colestid ® (colestipol hydrochloride), Lopid ® (gemfibrozil), Lorelco ® (probucol), Nicolar ® (niacin/nicotinic acid) and Questran ® (cholestyramine resin). These drugs, and the treatments in general, however, are directed only at the cause and not the result of atherosclerosis and have not been shown to be effective in reversing the plaque deposition and degenerative changes in the arterial walls. The pharmacologic agents also have many other shortcomings such as, for example, adverse side effects (hypertension, cardiac arrhythmias, gastrointestinal disturbances, headache, hypersensitivity, etc.), contraindications (heart, liver or kidney disease, pregnancy, etc.), requirement for lifelong conscientious administration, difficulty in maintaining consistent patient compliance, variable reliability and high cost.

Once the disease has progressed to the stage of significant persistent symptoms and compromised function, the next treatment step has conventionally been artery bypass grafting to repair and/or replace the damaged artery. While coronary artery bypass has become one of the more common major cardiovascular surgical procedures in the United States, surgery clearly is not the solution to the pathologic process since it has no arresting or reversing effect on the progress of the disease and only temporarily overcomes the most critically affected artery or arteries by bypassing them, if possible. Moreover, there is a significant risk of morbidity and mortality associated with surgery which many patients are reluctant to accept. Indeed, the disease may continue to progress even as the operation is being performed, and the autogenous veins or arteries used to bypass the disease impaired arteries undergo atherosclerosis changes postoperatively generally at a faster rate than the original, affected arteries. Furthermore, the conclusion reached by the Coronary-Artery Surgery Study (CASS) sponsored by the National Heart, Lung and Blood Institute (NHLBI) is that there is no overall statistical benefit in the survival rate or the rate of development of myocardial infarction between the surgically and medically treated groups of patients.

As an alternative to coronary bypass surgery, it has been suggested that certain medications and procedures may be used to treat the results of atherosclerosis and not just the cause. These treatments include chelation with ethylene diamine tetraacetic acid (EDTA) and percutaneous transluminal coronary angioplasty (PTCA). EDTA treatments, however, are still experimental, unproven and potentially as harmful as they are beneficial. PTCA treatments are invasive, of limited application and success and occasionally manifest lethal complications. Highly experimental intra-arterial laser beam plaque vaporization has limited application and requires an open operative approach to affected vessels.

It has now been surprisingly discovered that parenterally administered solutions comprising certain mixtures of biologically active amino acids are effective in both markedly reducing plasma cholesterol levels and arresting and reversing arterial plaque deposition and degenerative vascular changes associated with atherosclerosis.

Certain amino acid solutions have been parenterally administered intravenously during the past three to four decades for a variety of medical reasons. Total Parenteral Nutrition (TPN), or intravenous hyperalimentation, is now a widely accepted technique for management of nutritional and metabolic problems in patients whose absorption and assimilation of adequate or optimal nutritional substrates cannot or should not be achieved via the alimentary tract. Indeed, use of this technique, pioneered by the present inventor, has been successful in supporting normal growth and development in infants and in one child for more than fifteen years since birth.

Currently, a number of standard TPN solutions are commercially available in the United States, including those sold under the trade name TRAVOSOL® (Travenol Laboratories), FREAMINE® (McGaw Laboratories), AMINOSYN® (Abbott Laboratories) and NOVAMINE (Cutter Medical, Division of Miles Laboratories). These standard intravenous feeding solutions are designed to be nutritionally balanced, that is, they are formulated to provide all of the caloric, protein (amino acid), vitamin, mineral, water and trace element requirements of the average patient. The components of these solutions are also available in modular form, allowing the physician and pharmacist to formulate special solutions tailored to the specific needs of patients during the course of their management. Essential fatty acids and additional calories in the form of a lipid can also be administered separately intravenously as fortified emulsions of soybean or safflower oil in order to meet specific nutritional requirements. In patients with renal failure, hepatic failure or severe stress, special intravenous formulations of amino acids are also commercially available for infusion as an adjunct to the management of these conditions. For example, U.S. Pat. No. 3,832,465 describes an amino acid solution for nutritional use and U.S. Pat. No. 3,950,529 describes administration of amino acids to patients having liver disease.

No suggestion has been made, however, that parenterally administered biologically active amino acid solutions might be used to treat atherosclerosis, particularly with respect to the reversal of the detrimental complications associated with the disease.

It is, therefore, an object of the present invention to provide amino acid compositions and methods for treating atherosclerosis whereby not only the plasma cholesterol levels (contributing cause) are lowered, but also the plaque deposition and degenerative arterial changes (results) and secondary complications associated with the disease can be substantially arrested, reversed or even to a certain extent cured.

It is a further object of the present invention to provide amino acid compositions and methods for treating atherosclerosis which do not produce the many side effects of conventional drug treatments and can effectively decrease or even eliminate the need for major surgery or other interventional procedures in most atherosclerosis patients.

SUMMARY OF THE INVENTION

In accordance with the present invention, there are provided methods and substrate compositions for use in treating atherosclerosis, a disease characterized by the deposition of fatty substances in, and fibrosis of, the inner layer of an artery resulting in plaque deposition on and degenerative changes in an arterial wall. The methods and compositions of the present invention are particularly advantageous in that they work to both significantly lower plasma cholesterol levels and substantially arrest, reverse and, to a certain extent, even cure the arterial plaque deposition and degenerative vascular wall changes associated with atherosclerosis.

The compositions of the present invention comprise, in their overall concept, at least in part an active antiatherosclerotic agent which in turn comprises a mixture of biologically active (L-form) amino acids. This mixture more preferably comprises at least arginine and the branched chain amino acids, isoleucine, leucine and valine, with arginine preferably being present within the mixture in the greatest weight percentage based upon the total weight of the amino acids in the mixture. Even more preferably the mixture also includes lysine, methionine, phenylalanine, threonine, tryptophan and histidine. Most preferably, the mixture also includes alanine, proline, serine, tyrosine, glycine, glutamic acid, aspartic acid and cysteine.

The compositions of the present invention may also comprise, in addition to the amino acid mixture, other nutrients or additives such as vitamins, minerals, electrolytes, carbohydrates, antibiotics, anticoagulents and the like as required by the specific needs of a patient.

The compositions of the present invention are preferably administered parenterally in the form of an aqueous solution through a central venous catheter due to the hypertonic nature of the preferred aqueous solutions. The daily ration of the aqueous solution is further preferably administered continuously and constantly intraveneously by an intraveneous infusion pump.

The primary advantages of this invention over other methods of managing patients with atherosclerosis include the following: plasma cholesterol levels can be lowered more promptly and to a greater extent than heretofore achieved with any previous therapeutic modality; the degree and extent of atherosclerosis plaque regression is greater than has even been demonstrated previously; the duration of therapy required to reverse the atherosclerosis plaque is relatively short compared with the duration of time over which the plaque had originally developed; all of the solution ingredients are biologically active nutrient substrates with negligible toxicity or adverse side effects when administered in the proposed dosage ranges; the cost/effectiveness and cost/benefit ratios compare favorably with pharmacologic and surgical approaches to treating atherosclerosis; the therapy can be initiated and carried out entirely on an outpatient basis; and the method addresses and attacks the basic pathophysiology of atherosclerosis primarily and biochemically rather than pharmacologically or by dealing only with complications of atherosclerosis surgically.

These and other features and advantages of the present invention will be more readily understood by those skilled in the art from a reading of the following detailed description and examples with reference to the accompanying drawing.

DETAILED DESCRIPTION OF THE PREFERRED EMBODIMENT

Figure 1:
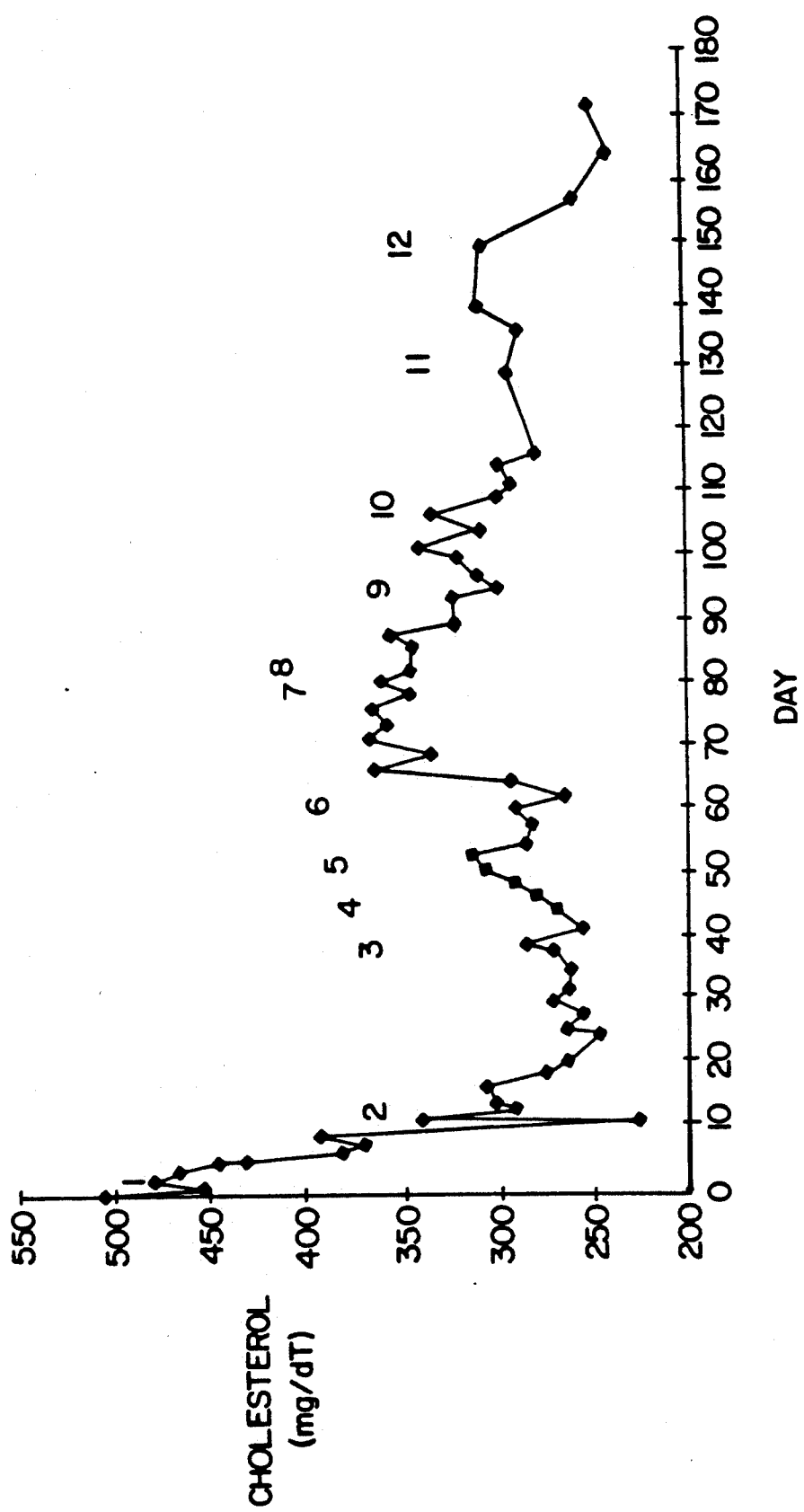
FIG. 1 is a graphical representation of the daily plasma total cholesterol levels of the human patient whose treatment is described in Example 2 demonstrating the responses elicited by changes in the formulation of the infusate.

The present invention provides methods and substrate compositions for treating atherosclerosis which, as previously mentioned is a disease characterized by the deposition of fatty substances, primarily cholesterol, as plaque and subsequent fibrosis in the inner layer (intima) of an artery. As also previously mentioned, atherosclerosis is believed to be related at least in part to plasma cholesterol and lipid levels. The compositions and methods of the present invention are particularly effective in both lowering plasma cholesterol levels (contributing cause) and also in reversing the arterial plaque deposition and degenerative changes (result) to substantially arrest, alleviate and, to a certain extent, even cure the many and varied problems, conditions and secondary complications associated with the disease.

The compositions of the present invention, in their overall concept, are comprised of biological substrates including at least, in part, an active antiatherosclerosis agent. Antiatherosclerosis, as used herein, refers to both the lowering of plasma cholesterol levels and the arrest and reversal of arterial plaque deposition and degenerative arterial wall changes. The active antiatherosclerosis agent, in the preferred embodiment, is a mixture of biologically active amino acids, preferably L-form amino acids.

Biologically active amino acids are generally classified as either essential or nonessential. Essential amino acids are those that cannot be synthesized within the body and must be ingested in adequate amounts in the diet. Non-essential amino acids, conversely, are those that can be synthesized biochemically within the body from other substrate sources. The amino acids most commonly classified as essential include isoleucine, leucine, lysine, methionine, phenylalanine, threonine, tryptophan and valine. The amino acids most commonly classified as non-essential include alanine, arginine, histidine, proline, serine, tyrosine, glycine, glutamic acid, aspartic acid and cysteine. Arginine and histidine have been classified as semiessential in that they appear to be essential for infants and to some extent in the presence of renal failure.

These biologically active amino acids also exist in dextrorotatory or D-form and levorotatory or L-form. The L-form is considerably more biologically active than the D-form and is, therefore, preferred for use as the antiatherosclerosis agent.

The substrate compositions of the present invention are placed in an aqueous solution which, in turn, is parenterally administered to a patient as the treatment. When so administered, the compositions of the present invention result in substantial lowering of plasma cholesterol levels and substantial reversal of the arterial plaque deposition on, and degenerative changes in, the arterial system.

The antiatherosclerosis agent preferably is a mixture of at least arginine, isoleucine, leucine and valine, preferably with arginine being present in the greatest weight percentage based upon the total weight of the biologically active amino acids in the mixture. These amino acids preferably comprise at least about 25% by weight of the amino acids present, but can, for brief infusion periods, be the sole active ingredients. The mixture may also include various of the other amino acids. Most preferably, all of the above-listed amino acids are present within the mixture to provide administration of all the amino acids along with other ingredients in a nutritionally balanced solution. All of these ingredients are a part of TPN solutions but, surprisingly, increased levels of the branched chain amino acids and arginine, often coupled with the reduction of amounts of histidine in the amino acid mixture, results in prompt (usually about one week) dramatic (usually 40% to 60%) reduction in plasma cholesterol. Also of note is the reduction of the simplest amino acids, particularly alanine and glycine, most particularly glycine, from TPN solutions.

The amino acids are included in the preferred amino acid mixtures in the approximate weight percentage ranges based upon the total weight of the amino acids in the mixture as set forth in Table I below.

TABLE I

| Amino Acid | Approximate Weight % | Amino Acid | Approximate Weight % |
|---|---|---|---|
| Isoleucine | 3–10 | Alanine | 2–20 |
| Leucine | 3–10 | Histidine | 1–4 |
| Lysine | 2.5–7.5 | Proline | 0–10 |
| Methionine | 2.5–7.5 | Serine | 0–8 |
| Phenylalanine | 3–10 | Tyrosine | 0–1 |
| Threonine | 1–4 | Glycine | 0–10 |
| Tryptophan | 1–3 | Glutamic Acid | 0–6 |
| Valine | 3–10 | Aspartic Acid | 0–6 |
| Arginine | 7–20 | Cysteine | 0–1 |

Note the non-essential amino acids listed above as being optional ingredients in the broad sense of this invention may contribute less to atherosclerosis recovery than the other species. The same may hold true for alanine and the non-branched chain essential amino acids. These amino acids, however, are important from a nutritional point of view when patient treatment extends over a period of months. As such, these amino acids may be added in greater or lesser amounts than listed above without materially affecting or altering the characteristics and advantages of the solution and, therefore, without departing from practicing the present invention. Thus, a more preferred amino acid mixture comprises of the following amino acids present in the following approximate weight percentages based upon the total weight of the amino acids in the mixture as set forth in Table II below.

TABLE II

| Amino Acid | Approximate Weight % | Amino Acid | Approximate Weight % |
|---|---|---|---|
| Isoleucine | 4–10 | Alanine | 7–16 |
| Leucine | 5–10 | Histidine | 1.5–3.5 |
| Lysine | 4.5–6.5 | Proline | 4.5–8.5 |
| Methionine | 3.5–5.5 | Serine | 2.5–6.5 |
| Phenylalanine | 4.5–7.5 | Tyrosine | 0–1 |
| Threonine | 2–3.5 | Glycine | 3–8 |
| Tryptophan | 1–2.5 | Glutamic Acid | 3.5–5.5 |
| Valine | 4–9 | Aspartic Acid | 2–4 |
| Arginine | 9–18 | Cysteine | 0–1 |

The amino acid mixtures are preferably accomplished by mixing the crystalline forms of the amino acids, usually the acetate, chloride and hydrochloride salt. A balance of the ions used in the salts is required to avoid upsetting the acid/base balance within the body of the patient; usually about 80% acetate and 20% chloride and hydrochloride. Usually the pH of the solution of the invention will range from about 5.0 to about 7.8 but preferably will be adjusted to the pH of blood, approximately 7.39, by the addition of a suitable non-toxic organic compound. The crystalline form of amino acid is preferred due to its high purity and the precise, reproducible formations which can be produced from such. Further, solutions made from the crystalline form can be directly assimilated into the body without preliminary biological action within the body. The mixture of amino acids can also be formulated using commercially available parenteral nutrition (TPN) solutions and adding amino acids, preferably in crystalline form, to achieve solutions of the invention. Preferred TPN solutions include those sold under the trademark Travasol®.

Additionally, the compositions of the present invention may include other essential nutrients such as vitamins, minerals, electrolytes, carbohydrates, antibiotics, anticoagulants and the like as required for nutritional, antibacterial and anticlotting purposes and other biological supports as will be recognized by one skilled in the art. As in substantially all biological applications, however, the most preferred compositions will be patient specific, that is, the actual amino acid mixture may be varied based upon a variety of factors which normally determine medication compositions and dosages such as, for example, the reaction of the specific patient to the composition; the tolerance of the specific patient to the individual and combined components; the stage and extent of the disease; the predominant organ(s) or system(s) adversely affected by the disease; the primary biologic functions adversely affected by the disease and/or its complications; the existance nature and extent of concomitant malnutrition, the comprehensive clinical symptom complex of the patient; the stage of the recovery and from surgical or other procedural attempts at alleviating signs and symptoms of the disease and/or its complications; the age, sex and general condition of the patient; the presence of other concomitant disorders (diabets mellitus, familial hyperlipidemia, etc.); and other factors as will be appreciated by those skilled in the art.

These factors are all related to the ability of a patient to utilize or tolerate the amino acid mixture and other components of the compositions of the present invention. In other words, each patient may require some adjustment of specific ingredients at various stages during the treatment as a result of one or more of the above-listed factors. For example, a diabetic may not be able to tolerate as high a caloric content in the form of a sugar as a person without diabetes. As another example, it is known that the amino acid requirements of a person with renal or liver failure are different from those of a person without these conditions. As still another example, a person suffering from malnutrition may require greater amounts of, and different, amino acids and other nutrients than a well-nourished person. One skilled in the art will be able to recognize these special needs and be able to adjust the compositions of the present invention accordingly.

Other adjustments to the amino acid mixture may be determined from blood and urine amino acid profiles. These profiles are indicative of how the body is utilizing a specific amino acid, and any deficiency or excess can be determined from such profiles and compensated for by altering the amino acid mixture. One skilled in the art will be able to make the desired adjustments accordingly once such an amino acid profile has been determined. The amino acid profile is adjusted in response to blood and urine analysis to determine the utilization of the amino acids by the body of the patient. It has been found that the antiatherosclerotic effect is largely determined by the amount of branched chain amino acids and arginine in the treatment. The significance of arginine as an important amino acid has heretofore been overlooked but, surprisingly, in the practice of this invention has emerged as an important contributor.

The compositions of the present invention are preferably administered parenterally in the form of an aqueous intravenous solution. The aqueous solution, therefore, comprises the composition as an additive solute in solution with an aqueous solvent base. The aqueous solvent base preferably comprises a sterile, ion-free water base to which may be added a variety of components depending upon the composition of the amino acid mixture and the specific needs of the individual patient. For example, if the composition does not have sufficient caloric value and the patient requires additional caloric intake, the aqueous solvent base may be a dextrose-water, fructose-water or invert sugar-water solution (equal parts of dextrose and fructose) including variable concentrations of the carbohydrate substrates chosen to meet the caloric needs of the patient. The solutions are compounded using established aseptic, antiseptic and pharmacochemical techniques well known to those skilled in the art to insure the complete solubility of the ingredients while maintaining the stability, sterility, safety and preferred formulation for the individual patients.

It is preferable that the active antiatheroscerotic agent, that is, the amino acid mixture, be present in solution in an effective amount which, when the solution is parenterally administered using hyperalimentation techniques well known to those skilled in the art, results in substantial lowering of plasma cholesterol and substantial reversal of arterial plaque deposition and degenerative arterial wall changes after a relatively short period of administration, usually within two to six months while at the same time providing the body of the patient nutrition necessary to sustain life. The amino acid mixture is present within the aqueous solution in concentrations ranging from as low as about 4 grams total weight of amino acids per 100 ml of solution (a 4% by weight solution) up to the solubility limits of the specific amino acid mixture within the particular aqueous solvent (sometimes as high as a 20% by weight in solution). Preferably, the amino acid mixture is present within the solution in concentrations ranging from about 7.5 to about 12 grams total weight of amino acids per 100 ml of solution (a 7.5% to 12% by weight solution). These concentrations will result in a hypertonic solution (800 to 1100 milliosmols per liter), that is, a solution having a higher osmotic pressure than blood (290 to 310 milliosmols per liter), the significance of which is discussed below. For the specific effective composition described above, it is preferable that the amino acid mixture be present in solution in a concentration of from about 9 to about 11, more preferably from about 10 to about 11, grams of amino acids per 100 ml of solution.

The aqueous solutions of the present invention are administered parenterally since the oral route has a number of disadvantages. When administered orally, the amino acids are subjected to the modifying digestive actions of the stomach, intestinal tract, pancreas and liver; the endogenous cycle exerts a buffering effect on the components of the formulation; the pattern of solutions to be administered is difficult to determine in order that the resultant blood levels of the active antiatherosclerosis agents be achieved identical to those induced by direct intravenous infusion; and methods of controlling precise levels of intake are difficult to establish and maintain. By parenteral administration, a direct assault can be launched against target tissues, and in some instances it is even possible to isolate a part of the body and perfuse it with the amino acid solution for hours, days or weeks without drastically altering the patient's normal nutritional patterns. Furthermore, parenteral administration permits constant, controlled administration, thus ensuring a continuity of effect without the nadirs or zeniths which inevitably occur following oral or enteral administration and subsequent absorption and assimilation.

Since the preferred aqueous solution will be hypertonic (about 800 to about 1100 milliosmols per liter), these solutions should be administered intravenously through a large diameter blood vessel having high blood flow for substantially instant dilution, most preferably through a central venous catheter inserted percutaneously into the superior vena cava by any one of several acceptable methods known to those skilled in the art. A particularly preferred method of catheter insertion is described in the article by O'Donnell, Clague and Dudrick entitled "Percutaneous Insertion of a Cuffed Catheter with a Long Subcutaneous Tunnel for Intravenous Hyperalimentation," published in Southern Medical Journal, Volume 76, No. 11 (1983), pages 1344–48, which is hereby incorporated by reference herein for all purposes as if fully set forth.

After catheterization has been achieved, continuous infusion of the aqueous antiatherosclerosis solution can begin. The total daily solution ration for the individual patient is preferably administered in an amount sufficient to provide the patient with between about 0.25 and about 3.5 grams amino acids, more preferably between about 1 and about 2 grams amino acids, per kilogram of body weight per 24-hour day. This solution ration is also preferably administered continuously and constantly intravenously by commercially available intravenous infusion pumps to maintain a consistent amino acid level within the body.

During the course of extended infusion therapy, generally from about two months to about eight months, the patient preferably will not ingest any additional nutrient substrates which can affect the amino acid balance or metabolism within the body. The patient will be allowed to drink non-nutrient fluids and to ingest whatever oral medications which may be required during the course of the therapy. In selected patients, it will be feasible to infuse the solution on an ambulatory or outpatient basis using portable lightweight pumps and custom made support apparatus for the solution, infusion tubing and pump. In even more highly selected patients, it may be preferable to infuse the entire daily ration of solution in 12-16 hours of the 24 hour day, allowing the patients to disconnect themselves from the pump and infusion apparatus for eight to twelve hours in order to increase their freedom and activities during the non-infusion periods. Whenever the patient is disconnected from the infusion tubing, it will be necessary to instill 1-2 ml of solution containing about 100 units heparin per ml into the central catheter and cap it with a sterile cap (for example, Luer-lock®) to prevent occlusion of the catheter with a blood clot.

During the first few weeks of infusion of the antiatherosclerosis solution, the patient should be monitored biochemically, hematologically and metabolically every 1-3 days via blood and urine specimens. Serum and/or urine amino acid profiles may be obtained from the specimens as desired and the amino acid mixtures adjusted accordingly. When initial stability of these indices has been achieved in response to the aqueous solution infusion and any indicated changes made in the initial composition of the solution, the intervals of monitoring can be extended to every 1-2 weeks.

Other indices to be monitored include the following: serum cholesterol, cholesterol esters, apolipoprotein $A_1$, apolipoprotein $B_{100}$, high density lipoprotein (HDL) cholesterol, triglycerides, sodium, potassium, chloride, bicarbonate, creatinine, calcium, inorganic phosphorus, glucose, urea nitrogen, uric acid, total protein, albumin, bilirubin, alkaline phosphatase, LDH, SGOT, SGPT, GGT, CPK, magnesium, zinc copper, blood prothrombin time, partial thromboplastin time, leukocyte count, erythrocyte count, hemoglobin, hemotocrit, mean corpuscular volume, mean corpuscular hemoglobin, mean corpuscular hemoglobin concentration, differential leukocyte count and platelet count. These standard tests are used individually, in various combinations and collectively to ensure the safety and efficacy of the treatment, to maintain homeostasis and to further assist the clinician in adjusting the solution specifically for the individual patient.

The foregoing detailed discussion of this invention will be further exemplified by the following specific examples offered by way of illustration and not limitation of the above described invention.

EXAMPLE 1

Attempts to implicate cholesterol as one of the primary etiologic agents in atherogenesis have been impaired somewhat by the inability to reduce and maintain lowered serum cholesterol levels by dietary and/or chemotherapeutic means alone. In a series of preliminary investigations, an animal model of atherosclerosis was developed over a period of several years by modifying the diet of New Zealand albino rabbits. Using several hundred male and female rabbits in a variety of studies while sequentially and logically modifying the diets, a consistent and reliable animal model was developed for inducing atherogenesis in these rabbits which simulated the distribution, various stages and severity, gross morphology and histologic characteristics, primary pathophysiology, secondary complications and clinical manifestations of atherosclerosis similar to that which has been observed and documented in human beings.

Rabbits, as herbivores, normally ingest only small quantities of dietary cholesterol. The inability of the rabbit livers of those rabbits to clear large quantities of dietary cholesterol biochemically resulted in a rapid increase in plasma cholesterol concentration, which in turn resulted in a reproducible degree, pattern and extent of atherosclerosis to advanced stages over a defined period of time proportional to the elevation in plasma cholesterol concentration and duration of the hypercholesterolemia.

As a result of the preliminary studies, an atherogenic diet was formulated and used to induce atherosclerosis in several hundred additional rabbits which were used as subjects in subsequent studies. In a typical study, 40 New Zealand albino adult male and female rabbits were all fed a basic laboratory rabbit diet (Teklad ® T.D. 82135) consisting of high fiber Purina ® Labchow 5326 fortified with 8% peanut oil by weight as the carrier for 2% crystalline cholesterol by weight. Within ten days to two weeks after initiation of this oral dietary regimen, the plasma total cholesterol levels rose to above 1000 mg/dL and were maintained between 1000 and 2000 mg/dL for the remainder of the six week atherogenic period.

At six weeks, ten rabbits were killed and autopsied in order to delineate and document the gross and microscopic severity, stage and extent of the disease in these animals as a baseline. The remaining 30 rabbits in the initial group were assigned randomly to one of three study groups. Group I consisted of ten animals which were continued on the atherogenic dietary regimen for an additional six weeks. Group II consisted of ten animals which received standard laboratory rabbit (Teklad ® T.D. 82135) diet without the peanut oil and crystalline cholesterol for six weeks. Group III consisted of ten animals which were infused continuously with an antiatherosclerosis solution for six weeks via a central venous catheter positioned in the superior vena cava in a manner known to those skilled in the art. The amino acid composition of the antiatherosclerotic solution containing 4.25% (by weight) amino acids and 25% (by weight) dextrose is listed below in Table III (Column A). The solution was administered to provide 1.5 grams of amino acids and 35 calories per kilogram body weight daily with vitamins, minerals and trace elements being added to achieve a balanced nutrient mixture.

TABLE III

| Amino Acid | Weight % A | Weight % B | Amino Acid | Weight % A | Weight % B |
|---|---|---|---|---|---|
| Isoleucine | 4.7 | 6.3 | Alanine | 20 | 15.8 |
| Leucine | 5.9 | 7.4 | Histidine | 4.1 | 3.2 |
| Lysine | 5.9 | 6.3 | Proline | 9.4 | 8.4 |
| Methionine | 5.9 | 5.3 | Serine | 7.0 | 6.3 |
| Phenylalanine | 5.9 | 6.3 | Tyrosine | 0.5 | 0.4 |
| Threonine | 3.5 | 3.2 | Glycine | 9.4 | 6.3 |
| Tryptophan | 2.4 | 2.1 | Glutamic Acid | — | 3.2 |
| Valine | 4.7 | 6.3 | Aspartic Acid | — | 2.1 |
| Arginine | 10.0 | 10.5 | Cysteine | 0.7 | 0.6 |

At the end of the second six week study period, all 30 rabbits were killed and autopsied to determine and delineate the severity, stage and distribution of atherosclerosis. In the Group I rabbits, complicated atherosclerosis lesions were induced which reproducibly and consistently involved approximately 85% to 95% of the aorta from its origin at the heart to the bifurcation of the common iliac arteries, with the pattern of superficial plaque and arterial wall distribution characteristic of atherosclerosis lesions observed in human beings. Several of the rabbits in Group I showed evidence of having sustained human-like myocardial infarctions, cerebral infarctions, intestinal ischemia and infarction, and ischemia and infarction in the hind extremities.

The rabbits in Group II which were fed the standard laboratory rabbit diet for the six weeks did not exhibit any regression of the atherosclerosis plaque when compared with the initial group of ten rabbits killed after six weeks on the atherogenic diet. Instead, there was slight progression of the atherosclerosis in Group II during this second six week period.

In the Group III rabbits receiving the special atherosclerosis intravenous formulation, however, dramatic regressions occurred in the atherosclerosis plaques. In fact, the aorta was about 90% free of any evidence of atherosclerosis. In response to plasma and urine amino acid concentrations measured at weekly intervals in the Group III rabbits, the daily intravenous amino acid ration was increased from 1.5 to 1.7 grams per kilogram body weight, and glutamic acid and aspartic acid were added to the formulation. The final amino acid composition for Group III rabbits is shown in Column B, Table III. Note that the greatest increases occurred in the branched chain amino acids in the composition while arginine was increased slightly. These experiments were repeated until a total of 200 rabbits were studied in each of the three groups with results consistent with those above.

This investigation demonstrates consistent atherosclerosis plaque regression as a result of intravenous amino acid management alone. These studies formed the basis and justification for progressing to subsequent investigations in human patients.

Chronologically, studies at this point were begun in human patients using the antiatherosclerosis solution of the same composition which was infused into the last set of forty rabbits.

EXAMPLE 2

A forty year old man with severe generalized atherosclerosis secondary to familial Type II hyperlipidemia previously treated at a lipid research clinic with a combination of low cholesterol/fat, low calorie (1400 calories) diet and cholestyramine was considered for treatment using the solutions of this invention. Even after five months of this prior treatment, the patient's plasma cholesterol level could only be reduced from a baseline of 496 mg/dL to 409 mg/dL (top normal plasma cholesterol level is 260 mg/dL) and the patient did not experience any relief of his symptoms detailed below. Within two weeks of voluntary cessation of this prior regimen, the plasma cholesterol returned to levels between 490 and 536 mg/dL.

The patient had recovered from a myocardial infarction one year earlier, but continued to have angina pectoris, could walk only one block without severe leg cramps and claudication, and had frequent fainting spells and numbness in his extremities related to poor blood flow in his major arteries. Four of the eight distal extremity pulses commonly palpated in the arms and legs were absent, and the remainder were diminished in strength by about 50%. Coronary angiography demonstrated complete occlusion of his right main coronary artery with diffuse narrowing and impaired blood flow in his left anterior descending and circumflex coronary arteries secondary to atherosclerosis. There was no evidence of significant collateral myocardial circulation, and because of the generalized diffuse extent of his disease, he was not a potential candidate for coronary artery bypass surgery.

His prognosis for life was less than two years. His plasma cholesterol concentration was 540 mg/dL, he was barely ambulatory and fainting spells had increased in frequency and severity so that he had fallen and injured himself on several occasions. Magnetic resonance imaging of his abdominal aorta, iliac arteries and carotid arteries confirmed up to 80% occlusion of the lumens of these vessels by atherosclerosis plaques. Doppler ultrasound studies of both lower extremities showed markedly diminished arterial blood flow bilaterally.

A percutaneous central venous catheter was inserted into the superior vena cava via the right subclavian vein and initially an intravenous solution having the amino acid composition as set forth in Column B, Table III, above, was infused continuously. The patient initially received 1.35 grams of amino acids per kilogram body weight or a ration of 95 grams of amino acids as this formulation. Simultaneously he received 35 calories per kilogram body weight as dextrose together with his daily requirements of vitamins, minerals and trace elements using standard intravenous additives. Baseline metabolic studies were obtained serially throughout the six month treatment and clinical study period. The patient was asked not to ingest any foodstuffs other than water throughout the study.

During the course of antiatherosclerosis infusion therapy and study in the patient, the initial solution formulation was modified on several occasions in response to the plasma cholesterol levels as illustrated in FIG. 1.

As can be seen in FIG. 1, the plasma cholesterol concentration dropped from the initial 508 mg/dL to 450 mg/dL within two days. At point 1, the total daily calories were reduced in the mixture from 2500 (35 cal/kg) to 2100 (30 cal/kg) because the relative inactivity of the patient did not merit the originally calculated caloric requirements. By the eighth day of therapy, the plasma cholesterol level had dropped further to 370 mg/dL, but rose to 393 mg/dL on the ninth day. At point 2, the daily dosages of the branched chain amino acids—leucine, isoleucine and valine—were increased by two grams. At this point, the following amino acids were present in the following approximate weight percentages based upon the total weight of the amino acids in the mixture: isoleucine, 7.9%; leucine, 8.9%; lysine, 5.9%; methionine, 5.0%; phenylalanine, 5.9%; threonine, 3.0%; tryptophane, 2.0%; valine, 7.9%; alanine, 14.9%; arginine, 9.9%; histidine, 3,0%; proline, 7.9%; serine, 5.9%; tyrosine, 0.4%; glycine, 5.9%; glutamic acid, 3.0%; aspartic acid, 2.0%; and cysteine, 0.6%. The amino acid dosage was increased from 1.35 to 1.45 grams per kilogram body weight per day for a daily total ration of 101.5 grams of amino acids as this formulation.

Within ten days of starting the therapy, the plasma cholesterol level had dropped dramatically to 220 mg/dL, representing a 57% reduction from the starting level of 508 mg/dL. At points 3, 4 and 5, minor changes in concentrations of various amino acid components and dextrose calories were made in response to biochemical determinations made on serum and urine specimens. More specifically, at point three the phenylalanine was increased by one gram and the glycine dose was decreased by one gram in the daily amino acid ration. At point four, the daily dextrose ration was increased to provide 35 cal/kg because the patient had increased his activity and began to lose weight. At point five, the alanine dose was decreased by three grams while the glutamic acid and aspartic acid dosages were each increased by 1.5 grams in the daily amino acid ration.

At point 6, a dramatic rise in the plasma cholesterol level from 260 to 370 mg/dL occurred following the intravenous infusion of a single 500 ml dose of 10% soybean oil emulsion (sold under the trademark Intralipid ®). Points 7 and 8 represent reductions in total calories administered as dextrose to 34 cal/kg and 33 cal/kg, respectively, the plasma cholesterol level remained significantly elevated above its pre-fat infusion nadir for at least four weeks after the infusion of the fat emulsion. By that time it had dropped back to 300 mg/dL, and at point 9, a single 500 ml dose of 20% soybean oil emulsion was given intravenously (Intralipid ®) with a rise in the serum plasma cholesterol level to 345 mg/dL, confirming the deleterious effect on the plasma cholesterol level of infusing even essential fatty acids as soybean oil emulsions. At point 10 the daily dextrose calories were reduced to 30 cal/kg, and the daily dosages of proline and serine were each decreased by two grams. Because the patient noted a loss of energy and weight, the glucose ration was restored to 35 cal/kg at point 11. At point 12, the arginine concentration was nearly doubled in the solution while the histidine was decreased. A significant drop in plasma cholesterol occurred from 306 mg/dL to 245 mg/dL. The amino acid mixture composition at this point is set forth in Table IV below. The amino acid dosage at this point was increased from 1.45 to 1.5 grams per kilogram body weight per day for a daily total ration of 103.5 grams of amino acids.

TABLE IV

| Amino Acid | Weight % | Mol % | Amino Acid | Weight % | Mol % |
|---|---|---|---|---|---|
| Isoleucine | 7.7 | 7.8 | Alanine | 11.6 | 17.0 |
| Leucine | 8.7 | 8.6 | Histidine | 2.4 | 1.5 |
| Lysine | 5.8 | 4.2 | Proline | 5.8 | 6.6 |
| Methionine | 4.8 | 4.3 | Serine | 3.9 | 4.8 |
| Phenylalanine | 6.8 | 5.3 | Tyrosine | 0.4 | 0.3 |
| Threonine | 2.9 | 3.2 | Glycine | 4.8 | 8.4 |
| Tryptophan | 1.9 | 1.3 | Glutamic Acid | 4.4 | 3.9 |
| Valine | 7.7 | 8.6 | Aspartic Acid | 3.4 | 3.3 |
| Arginine | 16.4 | 10.2 | Cysteine | 0.6 | 0.6 |

During the next week, coronary angiography, magnetic resonance imaging of his aorta, carotid arteries and iliac arteries and doppler ultrasound studies of both lower extremities were repeated. The treatment/study period was then terminated and the patient resumed oral feeding with a restriction of dietary cholesterol to 100 mg daily.

During the six months of treatment, the patient had no angina pectoris or fainting spells; three of the previously four absent extremity pulses could now be palpated; the four previously palpable extremity pulses increased in strength by 50 to 100%; the blood flow to his legs steadily increased up to 250-300% as demonstrated by resting doppler ultrasound studies, and he was able to walk up to 3–4 miles per day at four miles per hour without cramping or claudication in his legs.

At the end of the six month treatment period, magnetic resonance imaging demonstrated up to a 40–50% decrease in atherosclerosis plaque in the abdominal aorta, common iliac arteries and carotid arteries. Repeat coronary angiography demonstrated widely patent left anterior descending and circumflex coronary arteries, with multiple collateral arteries to the right coronary artery also widely patent except at the point of previous complete occlusion at its origin.

In addition to these dramatic demonstrations of atherosclerosis plaque regression and increased arterial blood flow through multiple previously compromised arteries, further evidence of improved bodily functions was manifested by the patient's ability to play 18 holes of golf while scoring in the 70's, and to gain employment as a carpenter with a housing construction firm. He has remained asymptomatic and active physically for more than 15 months since his therapy was initiated. Continued periodic observation and study occurred to document successful achievement of regression of atherosclerosis and improvement of arterial blood flow and bodily functions, as clearly demonstrated in this patient, are unprecedented with any form of medical or dietary management.

The final solution formulation which evolved during the course of the six month study period in this patient was subsequently infused into an additional ten rabbits as part of a supplementary group of forty rabbits studied in an otherwise identical manner as described above. The regression of atherosclerosis documented in this supplementary group of 10 rabbits was the most effective, consistent and complete of any of the animals studied and ranged from 98% to 99% disappearance of atherosclerotic disease.

EXAMPLE 3

Additional corroborative evidence of the effectiveness of the method and composition for treating atherosclerosis was obtained in 30 volunteer human subjects who had been receiving total parental nutrition via central venous feeding catheters for two months to eight years. Reductions of plasma cholesterol levels by 40–60% below their usual cholesterol levels regardless of the magnitude of the absolute values were achieved in all of the subjects within one week of changing the aqueous solution infusate to the amino acid compositions as set forth in either Table III or Table IV. These findings are highly significant not only because of the order of magnitude of the reductions in plasma choesterol levels documented in these subjects, but also because the positive response rate was 100%. All of these patients had been receiving long-term intravenous infusions of conventional TPN substrates containing mixtures of amino acids, without any significant reduction in plasma cholesterol levels. The infusate composition of Table IV caused dramatic reduction.

A striking example of the effectiveness of the solution described in Table IV in reducing plasma cholesterol levels in one patient occurred with the reduction of an already low baseline plasma cholesterol concentration of 83 mg/dL to 50 mg/dL within one week, representing a 40% reduction utilizing an aqueous solution having an amino acid composition as set forth in Table IV.

These data suggest that the mechanism of action of this invention is probably an active biochemical process rather than a result of severe restriction of dietary cholesterol, cholesterol precursors and other lipids, and demonstrate the effectiveness of the present invention.

The compositions and methods of the present invention, as previously described and as illustrated in the examples, provide a unique, potent and effective modality for the treatment of atherosclerosis. The recently completed National Institute of Health sponsored Lipid Research Clinic-Coronary Primary Prevention Trial was the first study in human beings to establish conclusively that lowering blood cholesterol levels reduces heart attacks and heart attack deaths. However, despite intensive dietary control and administration of pharmacologic plasma cholesterol reducing agents, the average plasma cholesterol level during the ten year study period was reduced by only 8.6% with no higher than a 19% reduction in the best responding patients. However, the incidence of myocardial infarctions in this study group was reduced by up to 19% when compared with the general population. The incidence of myocardial infarctions can be even more significantly reduced in association with the 40–60% reductions in plasma cholesterol levels which have been demonstrated with the use of this invention.

It should be noted that many modifications and variations besides the embodiments specifically mentioned may be made in the aforedescribed compositions and methods without departing substantially from the concept of the present invention. Accordingly, it should be clearly understood that the form of the invention described and illustrated herein is exemplary only and is not intended as a limitation upon the scope thereof.

I claim:

1. A method for lowering plasma cholesterol levels and reversing arterial plaque deposition and degenerative changes associated with atherosclerosis, comprising the step of parenterally administering a composition consisting essentially of a mixture of biologically active amino acids, said mixture comprising:

from about 3% to about 10% isoleucine
   from about 3% to about 10% leucine
   from about 2.5% to about 7.5% lysine
   from about 2.5% to about 7.5% methionine
   from about 3% to about 10% phenylalanine
   from about 1% to about 4% threonine
   from about 1% to about 3% tryptophan
   from about 3% to about 10% valine
   from about 2% to about 20% alanine
   from about 7% to about 20% arginine
   from about 1% to about 4% histidine
   from about 0% to about 10% proline
   from about 0% to about 8% serine
   from about 0% to about 1% tyrosine
   from about 0% to about 10% glycine
   from about 0% to about 6% glutamic acid
   from about 0% to about 6% aspartic acid
   from about 0% to about 1% cysteine by weight based upon the total weight of said biologically active amino acids in said mixture and the biologically active amino acids are present in their levorotatory form.

2. The method of claim 1, wherein arginine is present within said mixture in the greatest weight percentage based upon the total weight of said biologically active amino acids in said mixture.

3. The method of claim 1, wherein said biologically active amino acids comprise their crystalline form.

4. A method of treating atherosclerosis, a disease characterized by the deposition of fatty substances in and fibrosis of the inner layer of an artery resulting in plaque deposition on and degenerative changes in an arterial wall, comprising parenterally administering for an effective period of time an effective dose of an aqueous solution comprising an antiatherosclerotic agent to substantially lower plasma cholesterol levels and substantially reverse said plaque deposition and said degenerative changes, wherein said antiatherosclerotic agent comprises a mixture of biologically active amino acids including at least arginine, isoleucine, leucine, and valine.

5. The method of claim 4, wherein said mixture further comprises lysine, methionine, phenylalanine, threonine, tryptophan and histidine.

6. The method of claim 5, wherein said mixture further comprises alanine, proline, serine, tyrosine, glycine, glutamic acid, aspartic acid and cysteine.

7. The method of claim 4, wherein arginine is present within said mixture in the greatest weight percentage based upon the total weight of said biologically active amino acids in said mixture.

8. The method of claim 4, wherein said biologically active amino acids comprise their levorotatory form.

9. The method of claim 4, wherein said biologically active amino acids comprise their crystalline form.

10. The method of claim 4, wherein said mixture further comprises:
from about 3% to about 10% isoleucine
from about 3% to about 10% leucine
from about 2.5% to about 7.5% lysine
from about 2.5% to about 7.5% methionine
from about 3% to about 10% phenylalanine
from about 1% to about 4% threonine
from about 1% to about 3% tryptophan
from about 3% to about 10% valine
from about 2% to about 20% alanine
from about 7% to about 20% arginine
from about 1% to about 4% histidine
from about 0% to about 10% proline
from about 0% to about 8% serine
from about 0% to about 1% tyrosine
from about 0% to about 10% glycine
from about 0% to about 6% glutamic acid
from about 0% to about 6% aspartic acid
from about 0% to about 1% cysteine
by weight based upon the total weight of said biologically active amino acids in said mixture.

11. The method of claim 4, wherein said aqueous solution comprises a sterile, ion free water solution.

12. The method of claim 4, wherein said aqueous solution further comprises a non-amino acid caloric supplement.

13. The method of claim 4, wherein said antiatherosclerotic agent has a final concentration of at least about 4 grams of said biologically active amino acids per 100 milliliters of said aqueous solution.

14. The method of claim 4, wherein said antiatherosclerotic agent has a final concentration of from 7.5 to about 12 grams of said biologically active amino acids per 100 milliliters of said aqueous solution.

15. The method of claim 4, wherein said antiatherosclerotic agent has a final concentration from about 9 to about 11 grams of said biologically active amino acids per 100 milliliters of said aqueous solution.

16. The method of claim 4, wherein said aqueous solution is parenterally administered in an effective dose comprising from about 0.25 to about 3 total grams of biologically active amino acids per kg of body weight pr day.

17. The method of claim 16, wherein said aqueous solution is parenterally administered in an effective dose comprising from about 1 to about 2 total grams of biologically active amino acids per kg of body weight per day.

18. A method of treating and reversing the degenerative changes of atherosclerosis, a disease characterized by the deposition of fatty substances and fibrosis in the inner layers of an artery resulting in plaque deposition on and degenerative changes in an arterial wall, comprising the step of parenterally administering for an effective period of time an effective dose of an aqueous solution of an antiatherosclerotic agent comprising at least arginine, isoleucine, leucine and valine wherein arginine is present within said mixture in the greatest weight percentage based upon the total weight percentage of said biologically active amino acids in said mixture, to substantially reverse said plaque deposition and said degenerative changes, remove deposited plaque and where said antiatherosclerotic agent comprises a mixture of biologically active amino acids.

19. The method of claim 18, wherein said mixture further comprises lysine, methionine, phenylalanine, threonine, tryptophan and histidine.

20. The method of claim 19, wherein said mixture further comprises alanine, proline, serine, tyrosine, glycine, glutamic acid, aspartic acid and cysteine.

21. The method of claim 18, wherein said biologically active amino acids comprise their crystalline form.

22. The method of claim 18, wherein said mixture further comprises the following mixture of amino acids:
from about 3.5% to about 10% isoleucine
from about 3% to about 10% leucine
from about 2.5% to about 7.5% lysine
from about 2.5% to about 7.5% methionine
from about 3% to about 10% phenylalanine
from about 1% to about 4% threonine
from about 1% to about 3% tryptophan
from about 3% to about 10% valine
from about 2% to about 20% alanine
from about 7% to about 20% arginine
from about 1% to about 4% histidine
from about 0% to about 10% proline
from about 0% to about 8% serine
from about 0% to about 1% tyrosine
from about 0% to about 10% glycine
from about 0% to about 6% glutamic acid
from about 0% to about 6% aspartic acid
from about 0% to about 1% cysteine
by weight based upon the total weight of said biologically active amino acids in said mixture.

23. The method of claim 18, further comprising a non-amino acid nutrient supplement.

* * * * *